US012746341B1

(12) United States Patent
Vitello

(10) Patent No.: US 12,746,341 B1
(45) Date of Patent: Sep. 29, 2026

(54) TORQUE LIMITING TAMPER EVIDENT CAP

(71) Applicant: MEDICAL DEVICE ENGINEERING, LLC, Pompano Beach, FL (US)

(72) Inventor: Patrick Vitello, Pompano Beach, FL (US)

(73) Assignee: MEDICAL DEVICE ENGINEERING, LLC, Pompano Beach Beach, FL (US)

( * ) Notice: Subject to any disclaimer, the term of this patent is extended or adjusted under 35 U.S.C. 154(b) by 492 days.

(21) Appl. No.: 18/195,263

(22) Filed: May 9, 2023

Related U.S. Application Data

(60) Provisional application No. 63/339,938, filed on May 9, 2022, provisional application No. 63/339,941, filed on May 9, 2022.

(51) Int. Cl.
*A61M 5/32* (2006.01)

(52) U.S. Cl.
CPC ................................ *A61M 5/3202* (2013.01)

(58) Field of Classification Search
CPC ............. A61M 5/3202; A61M 5/3204; B65D 55/0863; B65D 55/08
See application file for complete search history.

(56) References Cited

U.S. PATENT DOCUMENTS

| | | | |
|---|---|---|---|
| 722,943 | A | 3/1903 | Chappell |
| 732,662 | A | 6/1903 | Smith |
| 1,678,991 | A | 7/1928 | Marschalek |
| 1,970,631 | A | 8/1934 | Sherman |
| 2,186,888 | A | 1/1940 | Tullar et al. |
| 2,277,936 | A | 3/1942 | Rosenblatt |
| 2,459,304 | A | 1/1949 | Blank |
| 2,477,598 | A | 8/1949 | Hain |
| 2,734,665 | A | 2/1956 | Flamm |
| 2,739,590 | A | 3/1956 | Yochem |

(Continued)

FOREIGN PATENT DOCUMENTS

| | | |
|---|---|---|
| CN | 110589435 | 12/2019 |
| DE | 202008018507 | 2/2015 |

(Continued)

OTHER PUBLICATIONS

Arai Tsugio, Pilfering Proof Cap, JPH082544—Jan. 9, 1996.

*Primary Examiner* — Deanna K Hall
(74) *Attorney, Agent, or Firm* — Malloy & Malloy, P.L.; Jennie S. Malloy

(57) ABSTRACT

A torque limiting and tamper evident cap assembly includes a tip cap, an outer cover shrouding the tip cap, and an inner ring disposed around the tip cap. The tip cap and inner ring are configured to rotate as a single unit when a torque is applied to the tip cap. The inner ring and outer cover are configured to support torque in one direction, allowing a user to tighten a syringe onto the tip cap. The inner ring will support a maximum tightening torque before slipping or breaking. The inner ring and outer cover are also configured to slip if an unscrewing motion is applied. The inner ring acts as a tamper evident feature as it becomes free floating within the outer cover when the tip cap is removed for the first time, thereby preventing the outer cover from being re-secured over the tip cap.

7 Claims, 4 Drawing Sheets

(56) References Cited

U.S. PATENT DOCUMENTS 2,811,283 A 10/1957 Bowen
2,823,674 A 2/1958 Yochem
2,834,346 A 5/1958 Adams
2,875,761 A 3/1959 Helmer et al.
2,888,015 A 5/1959 Hunt
2,952,255 A 9/1960 Hein, Jr.
3,122,280 A 2/1964 Goda
3,180,532 A 4/1965 Michel
3,245,567 A 4/1966 Knight
3,301,256 A 1/1967 Cowley
3,323,798 A 6/1967 Miller
3,364,890 A 1/1968 Andersen
3,368,673 A 2/1968 Johnson
3,489,268 A 1/1970 Meierhoefer
3,568,673 A 3/1971 Cowley
3,574,306 A 4/1971 Alden
3,598,120 A 8/1971 Mass
3,610,241 A 10/1971 LeMarie
3,674,181 A 7/1972 Marks et al.
3,700,215 A 10/1972 Hardman et al.
3,706,307 A 12/1972 Hasson
3,710,922 A 1/1973 Lanphere et al.
3,712,749 A 1/1973 Roberts
3,726,445 A 4/1973 Ostrowsky et al.
3,730,325 A 5/1973 Goodwin
3,747,751 A 7/1973 Miller et al.
3,850,329 A 11/1974 Robinson
3,872,867 A 3/1975 Killinger
3,904,033 A 9/1975 Haerr
3,905,375 A 9/1975 Toyama
3,937,211 A 2/1976 Merten
3,987,930 A 10/1976 Fuson
4,005,739 A 2/1977 Winchell
4,027,669 A 6/1977 Johnston et al.
4,043,334 A 8/1977 Brown et al.
4,046,145 A 9/1977 Choksi et al.
4,068,696 A 1/1978 Winchell
4,085,845 A 4/1978 Perfect
4,106,621 A 8/1978 Sorenson
4,216,585 A 8/1980 Hatter
4,216,872 A 8/1980 Bean
4,220,151 A 9/1980 Whitney
4,244,366 A 1/1981 Raines
4,252,122 A 2/1981 Halvorsen
4,271,972 A 6/1981 Thor
4,286,591 A 9/1981 Raines
4,286,640 A 9/1981 Knox et al.
4,313,539 A 2/1982 Raines
4,369,781 A 1/1983 Gilson et al.
4,420,085 A 12/1983 Wilson et al.
4,430,077 A 2/1984 Mittleman et al.
4,433,790 A 2/1984 Gibson
4,457,445 A 7/1984 Hanks et al.
4,482,071 A 11/1984 Ishiwatari
D277,783 S 2/1985 Beck
4,520,942 A 6/1985 Dwinell
4,521,237 A 6/1985 Logothetis
4,530,437 A 7/1985 Gray et al.
4,530,697 A 7/1985 Kuhlemann et al.
4,558,554 A 12/1985 Herbert
4,571,242 A 2/1986 Klien et al.
4,589,171 A 5/1986 McGill
4,608,646 A 8/1986 Goodrich et al.
4,664,259 A 5/1987 Landis
4,667,837 A * 5/1987 Vitello ................ A61M 5/5086
215/253
4,676,530 A 6/1987 Nordgren et al.
4,693,707 A 9/1987 Dye
4,726,483 A 2/1988 Drozd
4,735,617 A 4/1988 Nelson et al.
4,742,910 A 5/1988 Staebler
4,743,229 A 5/1988 Chu
4,743,231 A 5/1988 Kay et al.
4,744,455 A 5/1988 Dragotta et al.
4,753,345 A 6/1988 Goodsir et al.
4,760,847 A 8/1988 Vaillancourt
4,784,493 A 11/1988 Turcheck, Jr. et al.
4,813,564 A 3/1989 Cooper et al.
4,819,784 A 4/1989 Sticht
4,832,695 A 5/1989 Rosenberg et al.
4,834,706 A 5/1989 Beck et al.
4,842,592 A 6/1989 Caggiani et al.
4,844,906 A 7/1989 Hermelin et al.
4,863,451 A 9/1989 Marder
4,906,231 A 3/1990 Young
4,919,285 A 4/1990 Roof et al.
4,936,445 A 6/1990 Grabenkort
5,007,535 A 4/1991 Meseke et al.
5,009,323 A 4/1991 Montgomery et al.
5,024,323 A 6/1991 Bolton
5,049,129 A 9/1991 Zdeb et al.
5,057,093 A 10/1991 Clegg et al.
D323,392 S 1/1992 Bryne
5,078,696 A 1/1992 Nedbaluk
5,085,332 A 2/1992 Gettig et al.
5,090,564 A 2/1992 Chimienti
5,119,975 A 6/1992 Jemielita
5,133,454 A 7/1992 Hammer
5,135,496 A 8/1992 Vetter et al.
5,148,652 A 9/1992 Herzog
5,163,922 A 11/1992 McElveen, Jr. et al.
5,165,560 A 11/1992 Ennis, III et al.
5,230,429 A 7/1993 Etheredge, III
5,236,077 A 8/1993 Hoppmann et al.
5,267,983 A 12/1993 Oilschlager et al.
5,292,308 A 3/1994 Ryan
5,293,993 A 3/1994 Yates, Jr. et al.
5,295,599 A 3/1994 Smith
5,312,367 A 5/1994 Nathan
5,312,368 A 5/1994 Haynes
5,316,163 A 5/1994 von Schuckmann
5,328,466 A 7/1994 Denmark
5,328,474 A 7/1994 Raines
5,332,113 A 7/1994 Kusler, III et al.
5,356,380 A 10/1994 Hoekwater et al.
5,370,226 A 12/1994 Gollobin et al.
5,380,295 A 1/1995 Vacca
5,402,887 A 4/1995 Shillington
5,405,339 A 4/1995 Kohnen et al.
5,456,668 A 10/1995 Ogle, II
5,458,580 A 10/1995 Hajishoreh
5,468,224 A 11/1995 Souryal
5,474,178 A 12/1995 DiViesti et al.
5,484,413 A 1/1996 Gevorgian
5,505,705 A 4/1996 Galpin et al.
5,531,695 A 7/1996 Swisher
5,540,324 A 7/1996 Knapp
5,540,666 A 7/1996 Barta et al.
5,549,571 A 8/1996 Sak
5,558,648 A 9/1996 Shields
5,584,817 A 12/1996 van den Haak
5,588,239 A 12/1996 Anderson
5,611,445 A 3/1997 Kano et al.
5,617,954 A 4/1997 Kato et al.
5,624,402 A 4/1997 Imbert
5,662,233 A 9/1997 Reid
5,674,209 A 10/1997 Yarger
5,695,470 A 12/1997 Roussigne et al.
5,699,913 A 12/1997 Richardson
5,700,247 A 12/1997 Grimard et al.
5,702,374 A 12/1997 Johnson
5,706,985 A 1/1998 Feer
5,711,443 A 1/1998 Bennett
5,713,485 A 2/1998 Liff et al.
5,776,124 A 7/1998 Wald
5,785,691 A 7/1998 Vetter et al.
5,797,885 A 8/1998 Rubin
5,807,343 A 9/1998 Tucker et al.
5,829,589 A 11/1998 Nguyen et al.
D402,766 S 12/1998 Smith et al.
5,842,567 A 12/1998 Rowe et al.
5,876,381 A 3/1999 Pond et al.
5,883,806 A 3/1999 Meador et al.
5,884,457 A 3/1999 Ortiz et al.

(56) References Cited

U.S. PATENT DOCUMENTS

| | | | |
|---|---|---|---|
| 5,901,866 | A | 5/1999 | Storar |
| 5,902,269 | A | 5/1999 | Jentzen |
| 5,926,922 | A | 7/1999 | Stottle |
| 5,951,522 | A | 9/1999 | Rosato et al. |
| 5,951,525 | A | 9/1999 | Thorne et al. |
| 5,954,203 | A | 9/1999 | Marconi |
| 5,954,657 | A | 9/1999 | Rados |
| 5,957,166 | A | 9/1999 | Safabash |
| 5,957,314 | A | 9/1999 | Nishida et al. |
| 5,963,136 | A | 10/1999 | O'Brien |
| 5,983,596 | A | 11/1999 | Corniani et al. |
| 5,989,227 | A | 11/1999 | Vetter et al. |
| 5,993,437 | A | 11/1999 | Raoz |
| 6,000,548 | A | 12/1999 | Tsals |
| D419,671 | S | 1/2000 | Jansen |
| 6,021,824 | A | 2/2000 | Larsen et al. |
| 6,027,482 | A | 2/2000 | Imbert |
| 6,068,614 | A | 5/2000 | Kimber et al. |
| D430,293 | S | 8/2000 | Jansen |
| 6,112,951 | A | 9/2000 | Mueller |
| D431,864 | S | 10/2000 | Jansen |
| 6,126,640 | A | 10/2000 | Tucker et al. |
| 6,190,364 | B1 | 2/2001 | Imbert |
| 6,193,688 | B1 | 2/2001 | Balestracci et al. |
| 6,196,593 | B1 | 3/2001 | Petrick et al. |
| 6,196,998 | B1 | 3/2001 | Jansen et al. |
| 6,216,885 | B1 | 4/2001 | Guillaume |
| 6,235,376 | B1 | 5/2001 | Miyazaki et al. |
| 6,279,746 | B1 | 8/2001 | Hussaini et al. |
| 6,280,418 | B1 | 8/2001 | Reinhard et al. |
| 6,287,671 | B1 | 9/2001 | Bright et al. |
| 6,322,543 | B1 | 11/2001 | Singh et al. |
| 6,325,227 | B1 | 12/2001 | Ekkert |
| 6,338,200 | B1 | 1/2002 | Baxa et al. |
| 6,358,241 | B1 | 3/2002 | Shapeton et al. |
| 6,375,640 | B1 | 4/2002 | Teraoka |
| 6,394,983 | B1 | 5/2002 | Mayoral et al. |
| 6,439,276 | B1 | 8/2002 | Wood et al. |
| 6,485,460 | B2 | 11/2002 | Eakins et al. |
| 6,488,666 | B1 | 12/2002 | Geist |
| 6,491,665 | B1 | 12/2002 | Vetter et al. |
| 6,500,155 | B2 | 12/2002 | Sasso |
| 6,520,935 | B1 | 2/2003 | Jansen et al. |
| 6,540,697 | B2 | 4/2003 | Chen |
| 6,565,529 | B1 | 5/2003 | Kimber et al. |
| 6,581,792 | B1 | 6/2003 | Limanjaya |
| 6,585,691 | B1 | 7/2003 | Vitello |
| 6,592,251 | B2 | 7/2003 | Edwards et al. |
| 6,666,852 | B2 | 12/2003 | Niedospial, Jr. |
| 6,682,798 | B1 | 1/2004 | Kiraly |
| 6,726,652 | B2 | 4/2004 | Eakins et al. |
| 6,726,672 | B1 | 4/2004 | Hanly et al. |
| 6,764,469 | B2 | 7/2004 | Broselow |
| 6,796,586 | B2 | 9/2004 | Werth |
| 6,821,268 | B2 | 11/2004 | Balestracci |
| D501,549 | S | 2/2005 | McAllister et al. |
| 6,921,383 | B2 | 7/2005 | Vitello |
| 6,935,560 | B2 | 8/2005 | Andreasson et al. |
| 6,942,643 | B2 | 9/2005 | Eakins et al. |
| 6,961,638 | B2 | 11/2005 | Ouellette |
| 6,991,126 | B2 | 1/2006 | Jackel |
| 7,036,661 | B2 | 5/2006 | Anthony et al. |
| 7,055,273 | B2 | 6/2006 | Roshkoff |
| 7,100,771 | B2 | 9/2006 | Massengale et al. |
| 7,125,397 | B2 | 10/2006 | Woehr et al. |
| 7,141,286 | B1 | 11/2006 | Kessler et al. |
| 7,175,081 | B2 | 2/2007 | Andreasson et al. |
| 7,182,256 | B2 | 2/2007 | Andreasson et al. |
| 7,232,066 | B2 | 6/2007 | Anderasson et al. |
| 7,240,926 | B2 | 7/2007 | Dalle et al. |
| 7,258,222 | B2 | 8/2007 | Marti Sala et al. |
| 7,299,981 | B2 | 11/2007 | Hickle et al. |
| 7,367,964 | B2 | 5/2008 | Heinz et al. |
| 7,374,555 | B2 | 5/2008 | Heinz et al. |
| 7,404,500 | B2 | 7/2008 | Marteau et al. |
| 7,410,803 | B2 | 8/2008 | Nollert et al. |
| 7,425,208 | B1 | 9/2008 | Vitello |
| 7,437,972 | B2 | 10/2008 | Yeager |
| 7,438,704 | B1 | 10/2008 | Kawashima et al. |
| D581,046 | S | 11/2008 | Sudo |
| D581,047 | S | 11/2008 | Koshidaka |
| D581,049 | S | 11/2008 | Sudo |
| 7,482,166 | B2 | 1/2009 | Nollert et al. |
| D589,612 | S | 3/2009 | Sudo |
| 7,497,330 | B2 | 3/2009 | Anthony et al. |
| 7,503,453 | B2 | 3/2009 | Cronin et al. |
| 7,588,563 | B2 | 9/2009 | Guala |
| 7,594,681 | B2 | 9/2009 | DeCarlo |
| 7,608,057 | B2 | 10/2009 | Woehr et al. |
| 7,611,487 | B2 | 11/2009 | Woehr et al. |
| 7,632,244 | B2 | 12/2009 | Buehler et al. |
| D608,900 | S | 1/2010 | Giraud et al. |
| 7,641,636 | B2 | 1/2010 | Moesli et al. |
| D612,939 | S | 3/2010 | Boone, III et al. |
| 7,681,606 | B2 | 3/2010 | Khan et al. |
| 7,698,180 | B2 | 4/2010 | Fago et al. |
| 7,708,035 | B2 | 5/2010 | Windmiller |
| 7,735,664 | B1 | 6/2010 | Peters et al. |
| 7,748,892 | B2 | 7/2010 | McCoy |
| 7,762,988 | B1 | 7/2010 | Vitello |
| 7,766,919 | B2 | 8/2010 | Delmotte |
| 7,802,313 | B2 | 9/2010 | Czajka |
| 7,886,908 | B2 | 2/2011 | Farrar et al. |
| 7,918,830 | B2 | 4/2011 | Langan et al. |
| 7,922,213 | B2 | 4/2011 | Werth |
| 7,988,004 | B1 | 8/2011 | Marret et al. |
| 8,034,041 | B2 | 10/2011 | Domkowski et al. |
| 8,079,518 | B2 | 12/2011 | Turner et al. |
| 8,091,727 | B2 | 1/2012 | Domkowwski |
| 8,118,788 | B2 | 2/2012 | Frezza |
| 8,120,484 | B2 | 2/2012 | Chisholm |
| 8,128,605 | B2 | 3/2012 | Masi et al. |
| 8,137,324 | B2 | 3/2012 | Bobst |
| 8,140,349 | B2 | 3/2012 | Hanson et al. |
| 8,151,970 | B2 | 4/2012 | McDonald et al. |
| 8,231,585 | B2 | 7/2012 | Heinz et al. |
| 8,252,247 | B2 | 8/2012 | Ferlic |
| 8,257,286 | B2 | 9/2012 | Meyer et al. |
| 8,328,082 | B1 | 12/2012 | Bochenko et al. |
| 8,348,895 | B1 | 1/2013 | Vitello |
| 8,353,869 | B2 | 1/2013 | Ranalletta et al. |
| 8,413,410 | B2 | 4/2013 | Ulm et al. |
| 8,413,811 | B1 | 4/2013 | Arendt |
| 8,443,999 | B1 | 5/2013 | Reinders |
| D684,057 | S | 6/2013 | Kwon |
| 8,512,277 | B2 | 8/2013 | Del Vecchio |
| 8,528,757 | B2 | 9/2013 | Bisio |
| 8,556,074 | B2 | 10/2013 | Turner et al. |
| 8,579,116 | B2 | 11/2013 | Pether et al. |
| 8,591,462 | B1 | 11/2013 | Vitello |
| 8,597,255 | B2 | 12/2013 | Emmott et al. |
| 8,597,271 | B2 | 12/2013 | Langan et al. |
| 8,616,413 | B2 | 12/2013 | Koyama |
| D701,304 | S | 3/2014 | Lair et al. |
| 8,672,902 | B2 | 3/2014 | Ruan et al. |
| 8,702,674 | B2 | 4/2014 | Bochenko |
| 8,777,910 | B2 | 7/2014 | Bauss et al. |
| 8,777,930 | B2 | 7/2014 | Swisher et al. |
| 8,813,944 | B2 | 8/2014 | Tanner |
| 8,852,561 | B2 | 10/2014 | Wagner et al. |
| 8,864,021 | B1 | 10/2014 | Vitello |
| 8,864,707 | B1 | 10/2014 | Vitello |
| 8,864,708 | B1 | 10/2014 | Vitello |
| 8,911,424 | B2 | 12/2014 | Weadock et al. |
| 8,945,082 | B2 | 2/2015 | Geiger et al. |
| 8,978,909 | B2 | 3/2015 | Kakutani et al. |
| 8,985,305 | B2 | 3/2015 | Wong et al. |
| 9,016,473 | B2 | 4/2015 | Tamarindo |
| 9,027,769 | B2 | 5/2015 | Willows et al. |
| 9,082,157 | B2 | 7/2015 | Gibson |
| 9,095,667 | B2 | 8/2015 | Von Schuckmann |
| 9,101,534 | B2 | 8/2015 | Bochenko |
| D738,495 | S | 9/2015 | Strong et al. |
| 9,125,976 | B2 | 9/2015 | Uber, III et al. |

(56) References Cited

U.S. PATENT DOCUMENTS

| | | | |
|---|---|---|---|
| D743,019 | S | 11/2015 | Schultz |
| 9,192,443 | B2 | 11/2015 | Tennican |
| 9,199,042 | B2 | 12/2015 | Farrar et al. |
| 9,199,749 | B1 | 12/2015 | Vitello et al. |
| 9,220,486 | B2 | 12/2015 | Schweiss et al. |
| 9,220,577 | B2 | 12/2015 | Jessop et al. |
| 9,227,019 | B2 | 1/2016 | Swift et al. |
| D750,228 | S | 2/2016 | Strong et al. |
| 9,272,099 | B2 | 3/2016 | Limaye et al. |
| 9,311,592 | B1 | 4/2016 | Vitello et al. |
| D756,777 | S | 5/2016 | Berge et al. |
| 9,336,669 | B2 | 5/2016 | Bowden et al. |
| D759,486 | S | 6/2016 | Ingram et al. |
| D760,384 | S | 6/2016 | Niunoya et al. |
| D760,902 | S | 7/2016 | Persson |
| 9,402,967 | B1 | 8/2016 | Vitello |
| 9,427,715 | B2 | 8/2016 | Palazzolo et al. |
| 9,433,768 | B2 | 9/2016 | Tekeste et al. |
| 9,463,310 | B1 | 10/2016 | Vitello |
| D773,043 | S | 11/2016 | Ingram et al. |
| 9,480,801 | B2 | 11/2016 | Schiller et al. |
| D777,903 | S | 1/2017 | Schultz |
| 9,662,456 | B2 | 5/2017 | Woehr |
| D789,529 | S | 6/2017 | Davis et al. |
| 9,687,249 | B2 | 6/2017 | Hanlon et al. |
| 9,694,948 | B1 | 7/2017 | Pakhomov et al. |
| 9,744,304 | B2 | 8/2017 | Swift et al. |
| D797,928 | S | 9/2017 | Davis et al. |
| D797,929 | S | 9/2017 | Davis et al. |
| 9,764,098 | B2 | 9/2017 | Hund et al. |
| 9,821,152 | B1 | 11/2017 | Vitello et al. |
| D806,241 | S | 12/2017 | Swinney et al. |
| D807,503 | S | 1/2018 | Davis et al. |
| 9,855,191 | B1 | 1/2018 | Vitello et al. |
| D815,945 | S | 4/2018 | Fischer |
| 9,987,438 | B2 | 6/2018 | Stillson |
| D825,746 | S | 8/2018 | Davis et al. |
| 10,039,913 | B2 | 8/2018 | Yeh et al. |
| D831,201 | S | 10/2018 | Holtz et al. |
| D834,187 | S | 11/2018 | Ryan |
| 10,124,122 | B2 | 11/2018 | Zenker |
| 10,166,343 | B1 | 1/2019 | Hunt et al. |
| 10,166,347 | B1 | 1/2019 | Vitello |
| 10,183,129 | B1 | 1/2019 | Vitello |
| 10,207,099 | B1 | 2/2019 | Vitello |
| 10,207,835 | B2 | 2/2019 | Wilhelm et al. |
| D842,464 | S | 3/2019 | Davis et al. |
| D847,373 | S | 4/2019 | Hurwit et al. |
| 10,293,987 | B2 | 5/2019 | Sattig et al. |
| 10,300,263 | B1 | 5/2019 | Hunt |
| 10,307,548 | B1 | 6/2019 | Hunt et al. |
| 10,315,024 | B1 | 6/2019 | Vitello et al. |
| 10,315,808 | B2 | 6/2019 | Taylor et al. |
| 10,376,655 | B2 | 8/2019 | Pupke et al. |
| D859,125 | S | 9/2019 | Weagle et al. |
| 10,478,262 | B2 | 11/2019 | Niese et al. |
| 10,555,872 | B1 | 2/2020 | Thorne |
| 10,618,711 | B2 | 4/2020 | Weir |
| 10,695,490 | B2 | 6/2020 | Perazzo et al. |
| 10,758,684 | B1 | 9/2020 | Vitello et al. |
| 10,759,611 | B1 | 9/2020 | Kalm |
| 10,773,067 | B2 | 9/2020 | Davis et al. |
| 10,800,556 | B2 | 10/2020 | Thorne et al. |
| D903,865 | S | 12/2020 | Banik et al. |
| 10,888,672 | B1 | 1/2021 | Vitello |
| 10,898,659 | B1 | 1/2021 | Vitello et al. |
| 10,912,898 | B1 | 2/2021 | Vitello et al. |
| 10,933,202 | B1 | 3/2021 | Banik |
| 10,940,087 | B2 | 3/2021 | Thorne et al. |
| 10,953,162 | B1 | 3/2021 | Hunt et al. |
| 11,040,149 | B1 | 6/2021 | Banik |
| 11,040,154 | B1 | 6/2021 | Vitello et al. |
| 11,065,181 | B2 | 7/2021 | Davis et al. |
| 11,097,071 | B1 | 8/2021 | Hunt et al. |
| 11,168,818 | B2 | 11/2021 | Fangrow |
| 11,254,514 | B2 | 2/2022 | Vienot et al. |
| 11,278,681 | B1 | 3/2022 | Banik et al. |
| D948,713 | S | 4/2022 | Banik |
| 11,357,588 | B1 | 6/2022 | Vitello et al. |
| 11,413,406 | B1 | 8/2022 | Vitello et al. |
| 11,426,328 | B1 | 8/2022 | Ollmann et al. |
| 11,471,610 | B1 | 10/2022 | Banik et al. |
| 11,523,970 | B1 | 12/2022 | Vitello et al. |
| 11,541,180 | B1 | 1/2023 | Vitello et al. |
| 11,690,994 | B1 | 7/2023 | Banik et al. |
| 11,697,527 | B1 | 7/2023 | Hendren et al. |
| 11,779,520 | B1 | 10/2023 | Vitello |
| 11,793,987 | B1 | 10/2023 | Vitello et al. |
| 11,850,210 | B2 | 12/2023 | Dadachanji et al. |
| 11,857,751 | B1 | 1/2024 | Vitello |
| 11,872,187 | B1 | 1/2024 | Vitello et al. |
| 11,904,149 | B1 | 2/2024 | Vitello et al. |
| 11,911,339 | B1 | 2/2024 | Lehel et al. |
| 12,070,591 | B1 | 8/2024 | Vitello |
| 12,172,803 | B1 | 12/2024 | Vitello et al. |
| 12,195,241 | B1 | 1/2025 | Vitello et al. |
| 12,201,230 | B2 | 1/2025 | Bell |
| 12,383,463 | B1 | 8/2025 | Vitello et al. |
| 12,478,449 | B1 | 11/2025 | Vitello et al. |
| 12,545,483 | B1 | 2/2026 | Vitello et al. |
| 2001/0003150 | A1 | 6/2001 | Imbert |
| 2001/0034506 | A1 | 10/2001 | Hirschman et al. |
| 2001/0041866 | A1 | 11/2001 | Capes et al. |
| 2001/0056258 | A1 | 12/2001 | Evans |
| 2002/0007147 | A1 | 1/2002 | Capes et al. |
| 2002/0023409 | A1 | 2/2002 | Py |
| 2002/0046962 | A1 | 4/2002 | Vallans et al. |
| 2002/0079281 | A1 | 6/2002 | Hierzer et al. |
| 2002/0097396 | A1 | 7/2002 | Schafer |
| 2002/0099334 | A1 | 7/2002 | Hanson et al. |
| 2002/0101656 | A1 | 8/2002 | Blumenthal et al. |
| 2002/0104770 | A1 | 8/2002 | Shapeton et al. |
| 2002/0133119 | A1 | 9/2002 | Eakins et al. |
| 2002/0188259 | A1 | 12/2002 | Hickle et al. |
| 2003/0041560 | A1 | 3/2003 | Kemnitz |
| 2003/0055685 | A1 | 3/2003 | Cobb et al. |
| 2003/0146617 | A1 | 8/2003 | Franko, Sr. |
| 2003/0183547 | A1 | 10/2003 | Heyman |
| 2003/0187403 | A1 | 10/2003 | Balestracci |
| 2004/0008123 | A1 | 1/2004 | Carrender et al. |
| 2004/0011623 | A1 | 1/2004 | Sala |
| 2004/0064095 | A1 | 4/2004 | Vitello |
| 2004/0116858 | A1 | 6/2004 | Heinz et al. |
| 2004/0129738 | A1 | 7/2004 | Stukas |
| 2004/0173563 | A1 | 9/2004 | Kim et al. |
| 2004/0186437 | A1 | 9/2004 | Frenette et al. |
| 2004/0225258 | A1 | 11/2004 | Balestracci |
| 2005/0146081 | A1 | 7/2005 | MacLean et al. |
| 2005/0148941 | A1 | 7/2005 | Farrar et al. |
| 2005/0209555 | A1 | 9/2005 | Middleton et al. |
| 2006/0049948 | A1 | 3/2006 | Chen et al. |
| 2006/0084925 | A1 | 4/2006 | Ramsahoye |
| 2006/0089601 | A1 | 4/2006 | Dionigi |
| 2006/0169611 | A1 | 8/2006 | Prindle |
| 2006/0173415 | A1 | 8/2006 | Cummins |
| 2006/0189933 | A1 | 8/2006 | Alheidt et al. |
| 2007/0060898 | A1 | 3/2007 | Shaughnessy et al. |
| 2007/0106234 | A1 | 5/2007 | Klein |
| 2007/0142786 | A1 | 6/2007 | Lampropoulos et al. |
| 2007/0191690 | A1 | 8/2007 | Hasse et al. |
| 2007/0219503 | A1 | 9/2007 | Loop et al. |
| 2007/0257111 | A1 | 11/2007 | Ortenzi |
| 2008/0068178 | A1 | 3/2008 | Meyer |
| 2008/0078146 | A1 | 4/2008 | Cirio |
| 2008/0097310 | A1 | 4/2008 | Buehler et al. |
| 2008/0106388 | A1 | 5/2008 | Knight |
| 2008/0140020 | A1 | 6/2008 | Shirley |
| 2008/0243088 | A1 | 10/2008 | Evans |
| 2008/0302711 | A1 | 12/2008 | Windmiller |
| 2008/0303267 | A1 | 12/2008 | Schnell et al. |
| 2008/0306443 | A1 | 12/2008 | Neer |
| 2009/0008356 | A1 | 1/2009 | Gadzic et al. |
| 2009/0062744 | A1 | 3/2009 | Weilbacher et al. |
| 2009/0084804 | A1 | 4/2009 | Caspary et al. |

(56) References Cited

U.S. PATENT DOCUMENTS

| | | | |
|---|---|---|---|
| 2009/0099552 A1 | 4/2009 | Levy et al. | |
| 2009/0149815 A1 | 6/2009 | Kiel et al. | |
| 2009/0166311 A1 | 7/2009 | Claessens | |
| 2009/0212954 A1 | 8/2009 | Adstedt et al. | |
| 2009/0326481 A1 | 12/2009 | Swisher et al. | |
| 2010/0050351 A1 | 3/2010 | Colantonio et al. | |
| 2010/0051491 A1 | 3/2010 | Lampropoulos et al. | |
| 2010/0084403 A1 | 4/2010 | Popish et al. | |
| 2010/0089862 A1 | 4/2010 | Schmitt | |
| 2010/0126894 A1 | 5/2010 | Koukol et al. | |
| 2010/0179822 A1 | 7/2010 | Reppas | |
| 2010/0211016 A1 | 8/2010 | Palmer-Felgate | |
| 2010/0228226 A1 | 9/2010 | Nielsen | |
| 2010/0252564 A1 | 10/2010 | Martinez et al. | |
| 2010/0283238 A1 | 11/2010 | Deighan et al. | |
| 2010/0307108 A1 | 12/2010 | Sink et al. | |
| 2011/0009836 A1 | 1/2011 | Chebli et al. | |
| 2011/0044850 A1 | 2/2011 | Solomon et al. | |
| 2011/0046550 A1 | 2/2011 | Schiller et al. | |
| 2011/0046603 A1 | 2/2011 | Felsovalyi et al. | |
| 2012/0064515 A2 | 3/2012 | Knapp et al. | |
| 2012/0096957 A1 | 4/2012 | Ochman | |
| 2012/0110950 A1 | 5/2012 | Schraudolph | |
| 2013/0018356 A1 | 1/2013 | Prince et al. | |
| 2013/0018536 A1 | 1/2013 | Prince et al. | |
| 2013/0037383 A1 | 2/2013 | Iwasa et al. | |
| 2013/0056130 A1 | 3/2013 | Alpert et al. | |
| 2013/0088354 A1 | 4/2013 | Thomas | |
| 2013/0145725 A1 | 6/2013 | Bianco et al. | |
| 2013/0237949 A1 | 9/2013 | Miller | |
| 2013/0269592 A1 | 10/2013 | Heacock et al. | |
| 2014/0000781 A1 | 1/2014 | Franko, Jr. | |
| 2014/0034536 A1 | 2/2014 | Reinhardt et al. | |
| 2014/0069202 A1 | 3/2014 | Fisk | |
| 2014/0069829 A1 | 3/2014 | Evans | |
| 2014/0076840 A1 | 3/2014 | Graux et al. | |
| 2014/0135738 A1 | 5/2014 | Panian | |
| 2014/0155868 A1 | 6/2014 | Nelson et al. | |
| 2014/0163465 A1 | 6/2014 | Bartlett, II et al. | |
| 2014/0257843 A1 | 9/2014 | Adler et al. | |
| 2014/0319141 A1 | 10/2014 | Stratis et al. | |
| 2014/0326727 A1 | 11/2014 | Jouin et al. | |
| 2014/0353196 A1 | 12/2014 | Key | |
| 2014/0358078 A1 | 12/2014 | Fischer et al. | |
| 2015/0013811 A1 | 1/2015 | Carrel et al. | |
| 2015/0048045 A1 | 2/2015 | Miceli et al. | |
| 2015/0112296 A1 | 4/2015 | Ishiwata et al. | |
| 2015/0136632 A1 | 5/2015 | Moir et al. | |
| 2015/0182686 A1 | 7/2015 | Okihara | |
| 2015/0191633 A1 | 7/2015 | De Boer et al. | |
| 2015/0246185 A1 | 9/2015 | Heinz | |
| 2015/0251820 A1 | 9/2015 | Glaser et al. | |
| 2015/0298414 A1 | 10/2015 | Dittmer et al. | |
| 2015/0302232 A1 | 10/2015 | Strassburger et al. | |
| 2015/0305982 A1 | 10/2015 | Bochenko | |
| 2015/0310771 A1 | 10/2015 | Atkinson et al. | |
| 2016/0067144 A1 | 3/2016 | Chang | |
| 2016/0067422 A1 | 3/2016 | Davis et al. | |
| 2016/0090456 A1 | 3/2016 | Ishimaru et al. | |
| 2016/0136352 A1 | 5/2016 | Smith et al. | |
| 2016/0144119 A1 | 5/2016 | Limaye et al. | |
| 2016/0158110 A1 | 6/2016 | Swisher et al. | |
| 2016/0158449 A1 | 6/2016 | Limaye et al. | |
| 2016/0176550 A1 | 6/2016 | Viitello et al. | |
| 2016/0194121 A1 | 7/2016 | Ogawa et al. | |
| 2016/0250420 A1 | 9/2016 | Maritan et al. | |
| 2016/0279032 A1 | 9/2016 | Davis | |
| 2016/0328586 A1 | 11/2016 | Bowden et al. | |
| 2016/0361235 A1 | 12/2016 | Swisher | |
| 2016/0367439 A1 | 12/2016 | Davis et al. | |
| 2017/0007771 A1 | 1/2017 | Duinat et al. | |
| 2017/0014310 A1 | 1/2017 | Hyun et al. | |
| 2017/0124289 A1 | 5/2017 | Hasan et al. | |
| 2017/0173321 A1 | 6/2017 | Davis et al. | |
| 2017/0203086 A1 | 7/2017 | Davis | |
| 2017/0225843 A1 | 8/2017 | Glaser et al. | |
| 2017/0239141 A1 | 8/2017 | Davis et al. | |
| 2017/0297781 A1 | 10/2017 | Kawamura | |
| 2017/0319438 A1 | 11/2017 | Davis et al. | |
| 2017/0328758 A1 | 11/2017 | Fuchs | |
| 2017/0349335 A1 | 12/2017 | Sattig et al. | |
| 2017/0354792 A1 | 12/2017 | Ward | |
| 2018/0001540 A1 | 1/2018 | Byun | |
| 2018/0014998 A1 | 1/2018 | Yuki et al. | |
| 2018/0064604 A1 | 3/2018 | Drmanovic | |
| 2018/0078684 A1 | 3/2018 | Peng et al. | |
| 2018/0089593 A1 | 3/2018 | Patel et al. | |
| 2018/0098915 A1 | 4/2018 | Rajagopal et al. | |
| 2018/0147115 A1 | 5/2018 | Nishioka et al. | |
| 2018/0236177 A1 | 8/2018 | Schraga | |
| 2018/0312305 A1 | 11/2018 | Rognard | |
| 2019/0275313 A1* | 9/2019 | Godin | A61M 39/20 |
| 2019/0308006 A1 | 10/2019 | Erekovcanski et al. | |
| 2019/0388626 A1 | 12/2019 | Okihara | |
| 2021/0228445 A1 | 7/2021 | Bouteloup et al. | |
| 2021/0244892 A1 | 8/2021 | Maritan et al. | |
| 2022/0008645 A1 | 1/2022 | Ukai et al. | |
| 2022/0024630 A1 | 1/2022 | Bohamed | |
| 2022/0257467 A1 | 8/2022 | Yano et al. | |
| 2022/0296470 A1 | 9/2022 | Wagner | |
| 2022/0339067 A1 | 10/2022 | Christine et al. | |
| 2023/0036805 A1 | 2/2023 | Rey | |

FOREIGN PATENT DOCUMENTS

| | | |
|---|---|---|
| DE | 102020123373 | 3/2020 |
| DE | 102020123392 | 3/2022 |
| DE | 102020131870 | 6/2022 |
| EP | 0148116 | 7/1985 |
| EP | 269920 | 6/1988 |
| EP | 571980 | 12/1993 |
| EP | 2724977 | 4/2014 |
| EP | 2937616 | 10/2015 |
| GB | 486367 | 6/1938 |
| GB | 2102774 | 2/1983 |
| JP | 08002544 | 1/1996 |
| JP | 2014076618 | 5/2014 |
| KR | 101159987 | 6/2012 |
| KR | 101868822 | 6/2018 |
| WO | WO8607040 | 12/1986 |
| WO | WO9118801 | 12/1991 |
| WO | WO1992003348 | 3/1992 |
| WO | WO2008000279 | 1/2008 |
| WO | WO2017086607 | 5/2015 |
| WO | WO2025003684 | 1/2025 |

* cited by examiner

TORQUE LIMITING TAMPER EVIDENT CAP

CLAIM OF PRIORITY

This application claims the benefit, under 35 U.S.C. § 119, to two provisional patent applications, having Ser. Nos. 63/339,941 and 63/339,938, both of which were filed on May 9, 2022, and which are fully incorporated herein, by reference.

BACKGROUND OF THE INVENTION

Field of the Invention

The invention is related to tamper evident caps for syringes or other medical devices which limit the amount of torque that can be transmitted through the cap for purposes of preventing over tightening and to provide a tamper resistant feature.

DESCRIPTION OF THE RELATED ART

In the medical field, it is a relatively common procedure for authorized medical personnel to order that a patient be given a drug or medication by injection or other procedures, including administering fluids to a patient by intravenous (IV) infusion. It is also relatively common procedure for a number of administering devices to be pre-loaded or filled by a pharmacist, compounder, or other authorized personnel whether within the hospital or at another facility and location, which may be generally referred to as a filling station. However, a filling station is typically located in a remote part of the facility, relative to the patient care area where the injection is to be administered. Indeed, at large medical facilities, a filling station may resemble a factory on the hospital grounds from which drugs and other fluids are delivered to multiple nursing stations at different locations. Because of the remote location of many nurse's stations, relative to a filling station, a fluid or drug loaded administering device is very often given to another person for delivery to a nurse's station for subsequent dosing of the patient by a duly qualified nurse or other medically trained person. Also, and especially in the case where a drug has been prescribed and loaded in the administering device that is a very expensive or addictive, such as but not limited to morphine, there is a danger that the pre-loaded syringe or other administering device will be tampered with at some point, by a person seeking unauthorized access thereto. This possibility can present real danger in that if such person were to gain access to the prescribed medicine and then, inappropriately and without concern, substitute some other, unauthorized material in the syringe which looks like the actual prescribed medicine and dosage. By way of an example only, if saline solution were substituted for a dose of morphine or numerous other drugs, the result can be extremely serious. Thus, there is a problem of knowing if a sealed, preloaded syringe or other administering device has, or has not, been exposed to contamination or might otherwise have been compromised. This and related types of problems have been described in one or more previously granted U.S. patents granted to one of the inventors herein, such as U.S. Pat. No. 5,328,474.

Furthermore, with known or conventional closure assemblies, it is sometimes difficult to sufficiently tighten the closure assembly on the medical connector associated with the medical device, even though this is necessary to prevent leakage of the medicine from a discharge port or other portions of the medical connector. On the other hand, it is undesirable to "over-tighten" a closure assembly on a medical connector as it may result in some discomfort and/or inconvenience to personnel, having to repeatedly detach closure assemblies over a shift. There is a need in the art to resolve these and other problems.

SUMMARY OF THE INVENTION

While the disclosure of this application is largely demonstrated by the use of the inventive tamper evident cap as a closure for a syringe tip, it will be appreciated that the present invention May be adapted to any kind of medical connector, such as, but certainly not limited to, male or female luer tapers, enteral connectors, neuraxial connectors, intravenous fluid bags, as well as other connector structures utilized in the medical field and related arts.

According to one or more preferred embodiments of the invention, the tamper evident cap includes structuring operative to effectively limit or partially control the amount of torque force applied to the tamper evident cap when connected to a syringe. Such effective limiting or control of torque force will result in the cap being attached to the syringe with sufficient tightness to prevent leakage and stop fluid flow from the medical connector. In addition, the structural and operational versatility of the various embodiments of the tamper evident cap of the present invention also prevents excessive torque being applied to the closure assembly thereby restricting the possibility of "over-tightening" the closure assembly on the syringe.

Therefore, at least one embodiment of the present invention includes a biased, one-way drive assembly in which a tip cap (attached to the syringe) interacts with the outer cover (shrouding the tip cap) via biased fingers that engage with receiving structure on the inner periphery of the outer cover. When rotated in a tightening direction, the biased fingers engage the receiving structure in torque supporting relation to permit tightening of the syringe onto the tip cap. In a most preferred embodiment, the biased fingers are configured to slip or deflect upon reaching a recommended tightening specification for the syringe, thereby preventing over-tightening. In order to provide a tamper resistant feature, the biased fingers can be further configured such that, when the syringe is rotated in a loosening direction, the biased fingers slip against the receiving structure and do not transmit sufficient torque to loosen the tip cap from the syringe. In a most preferred embodiment, the outer cover includes a repeating "ramp-and-cliff" structure, while the biased fingers are cantilevered from the tip cap in a direction that opposes the cliffs when rotated in a tightening direction, but slips on the ramps when rotated in a loosening direction. Additionally, in a most preferred embodiment, the biased fingers project from an inner ring that is mounted on the tip cap, for reasons that will be discussed below.

In an alternative embodiment, the tip cap is configured to interact with the outer cover via one or more frangible members that are dimensioned and configured, taking into account the material from which they are made, to break when sufficient tightening torque is reached, resulting in an inability to continue tightening, as well as loosening, the tip cap from the syringe. In a most preferred embodiment, the frangible members are included within an inner ring that is mounted on the tip cap.

In either event, the torque limiting features may provide an "audible indication" to the user. The user will hear the biasing fingers passing over the cliffs in one embodiment, or the snap of the frangible members in another embodiment. Therefore, upon a user detecting such sound or "audible indication" the user will be made aware that sufficient "tightening force" has been exerted on the tamper evident cap.

A tamper evident feature can be accomplished by inserting an inner ring between the tip cap and the outer cover. For efficiency in manufacturing, the inner ring may also bear the torque-limiting features discussed above. However, in a preferred embodiment, the inner ring is restricted in its capacity to move within the outer cover. This function serves to secure the outer cover to the tip cap until the tip cap is removed from the outer cover, leaving the inner ring trapped but free floating within the outer cover. The invention may be further dimensioned and configured to limit a user's ability to reinstall the tip cap within the inner ring, thereby precluding one from reinstalling the outer cover altogether. This function serves as a clear indicator that the tip cap has been removed from the outer cover alerting the user to the possibility that the syringe has been compromised. In a most preferred embodiment, the outer cover includes a shoulder against which the inner ring rests when in an operative configuration. The inner ring and tip cap can also be mated in an interference fit, such that an easily determined and distinguished amount of force is required to draw the tip cap from the inner ring. Thus, when removing the outer cover to expose the tip cap, the user will draw the inner ring against the shoulder of the outer cover, which will serve to restrict further movement of the inner ring as the tip cap is drawn from the outer cover. Once the tip cap is completely removed, the inner ring will be free floating within the outer cover. Should an attempt be made to reinstall the outer cover, it will not be possible to reinstall the inner ring around the tip cap. Therefore, the outer cover will not be secure on the tip cap, serving as a tamper indicator.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
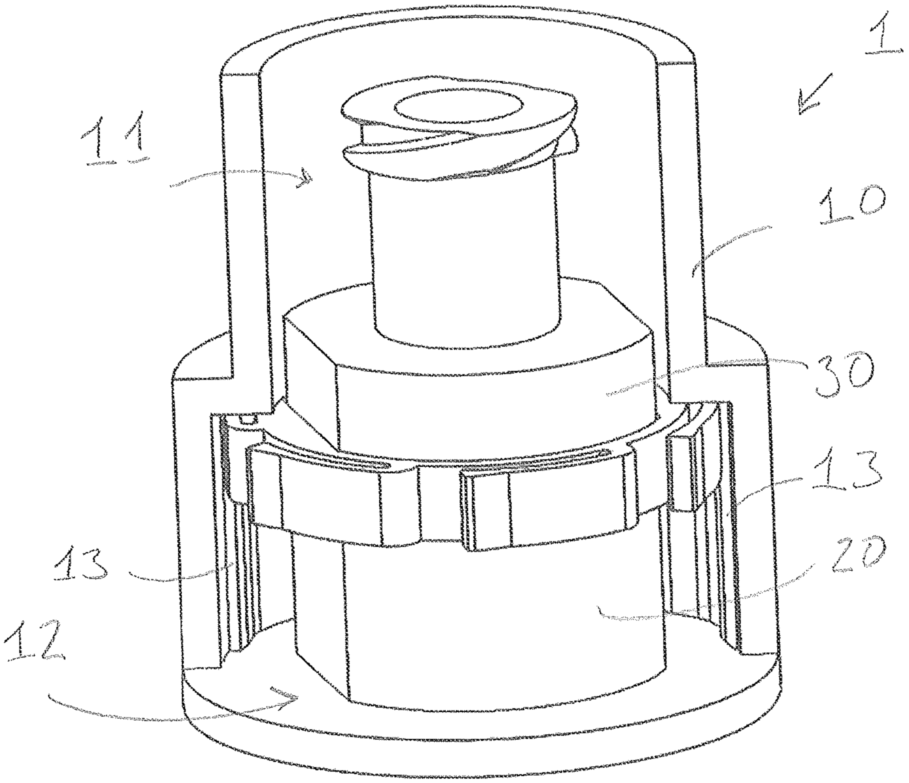
FIG. 1 is a partial cutaway view of a tamper evident cap according to one embodiment of the present invention.
Figure 2:
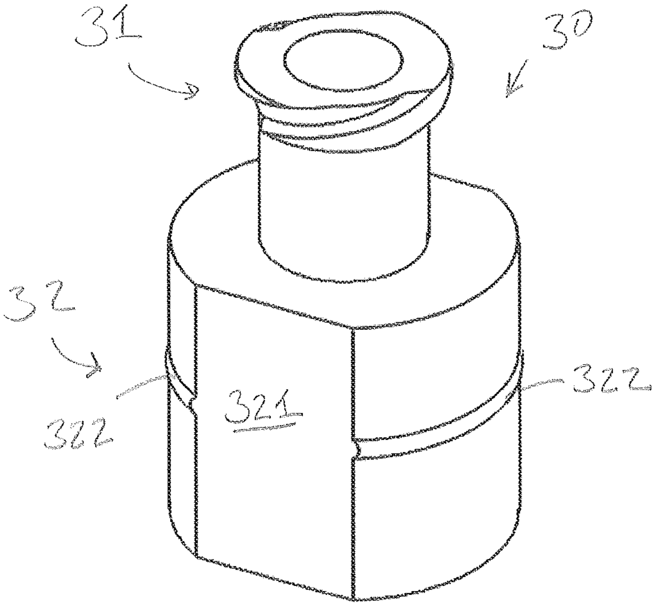
FIG. 2 is a perspective view of a tip cap in accordance with one embodiment of the present invention.
Figure 3:
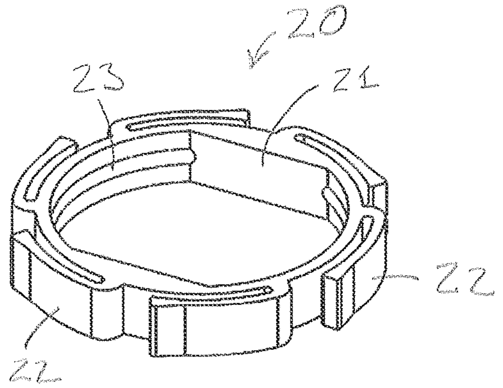
FIG. 3 is a perspective view of an inner ring according to one embodiment of the present invention.

Referencing FIGS. 1-3, the tamper evident cap 1 of the disclosed embodiment includes three primary components, an outer cover 10, an inner ring 20, and a tip cap 30. The tip cap 30 is designed to receive a syringe and, as such, includes a tip engaging portion 31 that may comprise any of a variety of configurations. In the depicted embodiment, the tip engaging portion 31 is shown as a standard locking style luer taper, but other types of connections may be used, such as a slip style luer taper or other known medical connection types. The tip cap 30 may also including an inner ring engaging portion 32 which is dimensioned and configured to receive the inner ring 20 about its circumference. In a preferred embodiment, the inner periphery of the inner ring 20 and the outer periphery of the tip cap 30 are cooperatively dimensioned and configured with one another such that when the tip cap 30 is rotated, the inner ring 20 can also rotate. In the depicted embodiment, both peripheries are substantially circular with the exception of one or more flats 21, 321 which, when aligned with one another, permit the tip cap 30 and inner ring 20 to rotate as a single unit.

The outer cover 10 may include a tip receiving portion 11 and a ring engaging portion 12. In the depicted embodiment, the diameter of the tip receiving portion 11 is smaller than the diameter of the ring engaging portion 12, resulting in a shoulder 14 that restricts translation of the inner ring 20 out of the outer cover 10. The ring engaging portion 12 may also include one or more ring engaging members 13 which are dimensioned and configured to be driven by corresponding structure on the inner ring 20. In the depicted embodiment, the inner ring 20 includes a plurality of biased fingers 22 dimensioned and configured to engage the ring engaging members 13 and permit torque to be transmitted from the tip cap 30, through the inner ring 20, to the outer cover 10 and vice-versa. As such, a user may secure the tamper evident cap 1 to a syringe by grasping the outer cover 10, inserting a syringe onto the tip engaging portion 31, and twisting the outer cover 10 relative to the syringe.

Figure 4:
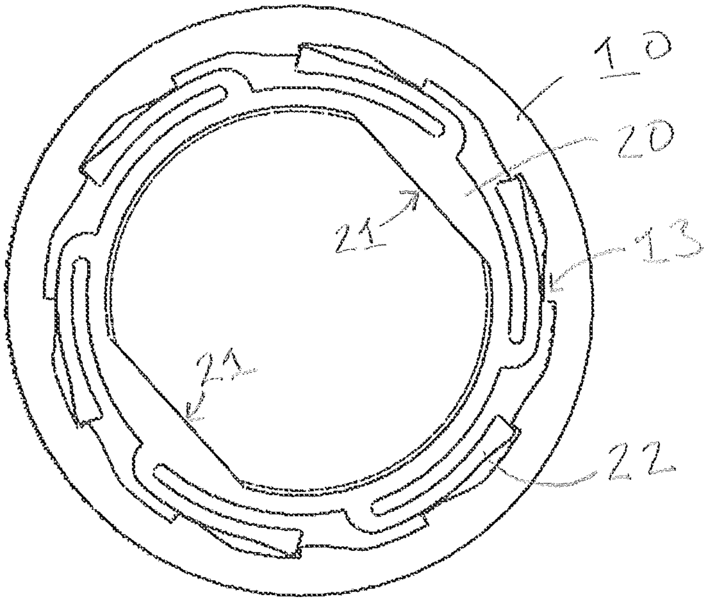
FIG. 4 is a bottom view an inner ring interacting with an outer cover according to one embodiment of the present invention.
Figure 5:
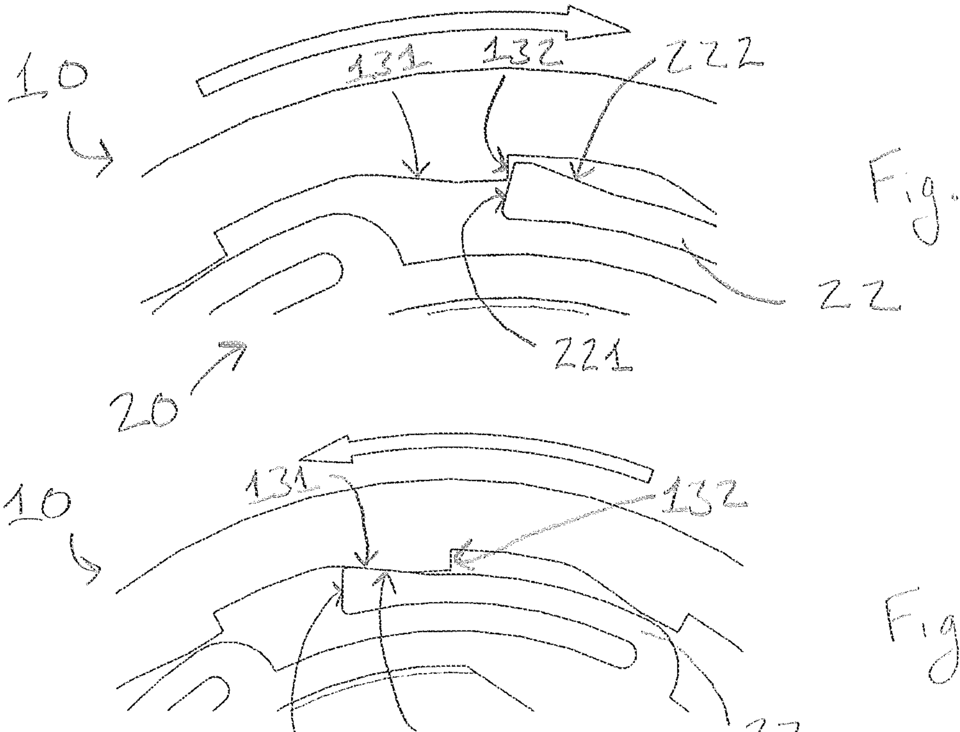
FIG. 5 is a detail view of an inner ring interacting with an outer cover according to one embodiment of the present invention.
Figure 6:
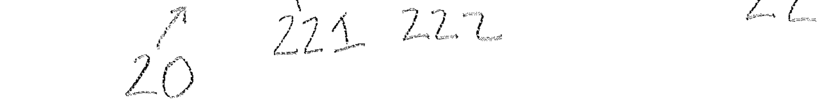
FIG. 6 is a detail view of an inner ring interacting with an outer cover according to one embodiment of the present invention.

In a most preferred embodiment, the tamper evident cap 1 is configured to transmit up to a certain amount of torque before slipping to prevent over tightening and may further be designed to slip at a comparatively low torque when the outer cover 10 is turned in a loosening direction, thereby preventing removal of the tamper evident cap 1 by unscrewing. FIGS. 4-6 depict one preferred embodiment for accomplishing such functionality. As can be seen, the biased fingers 22 are configured to protrude from the inner ring 20 in a cantilevered configuration thereby providing a natural spring force when the inner ring 20 is made of a sufficiently resilient material. The biased fingers 22 may also be configured with an acute face 222 and an obtuse face 221. In a most preferred embodiment, the acute face 222 may rise from the biased finger 22 at an angle of between approximately 180 degrees to approximately 150 degrees; the obtuse face 221 may be configured at an angle of between 90 degrees to approximately 75 degrees relative to the surface of the biased finger 22.

The outer cover 10 includes a plurality of ring engaging members 13, which in the depicted embodiment include a ramp 131 and cliff 132 construction oriented such that the cliff 132 faces meet with the obtuse faces 221 and the ramp 131 faces meet with the acute faces 222. As such, the arrangement can support the transmission of a certain amount of torque in one direction, but slip at a much lower torque application in the other direction. As shown in FIG. 5, when the outer cover 10 is rotated in the direction of the arrow, a first direction or a tightening direction, the cliffs 132 will engage against the obtuse faces 221. Because the included angle between the cliffs 132 and obtuse faces 221 is relatively steep, the arrangement can easily support torque transmission between the outer cover 10 and inner ring 20 without the biasing fingers 22 deflecting out of the way. However, in a most preferred embodiment, the angle at which the cliffs 132 and obtuse faces 221 meet can be designed to support a maximum recommended tightening torque of the syringe on the tip cap before the faces slip and the biased fingers 22 deflect out of the way, thereby preventing the user from over tightening the syringe on the tip cap. Accordingly, the biased fingers 22 can be dimensioned and configured to deflect away from said ring engagement members 13 upon reaching a predetermined minimum torque value when rotating the tip cap in a first direction.

On the other hand, when the outer cover 10 is rotated in the direction of the arrow shown in FIG. 6, a second direction or a loosening direction, then the acute faces 222 engage against the ramps 131. As such, the biased fingers 22 will not be able to support as much torque as when the outer cover is rotated in the other direction because the biased fingers 22 will deflect on a much lower application of force as compared to when the obtuse faces 221 are driven by the cliffs 132. In a most preferred embodiment, the angle at which the acute faces 222 meet the ramps 131 can be configured such that the torque supported by the biased fingers 22 before they deflect out of the way is substantially lower than the torque required to unscrew the syringe from the tip cap. Accordingly, the biased fingers 22 can be dimensioned and configured to deflect away from said ring engagement members 13 upon reaching a predetermined maximum torque value when rotating the tip cap in a second direction, wherein the predetermined maximum torque value (when rotating in the second or loosening direction) is less than the predetermined minimum torque value (when rotating in the first or tightening direction). Such an arrangement ensures that the tamper evident cap of the present invention may not be simply unscrewed from the syringe once it has been applied.

Figure 7:
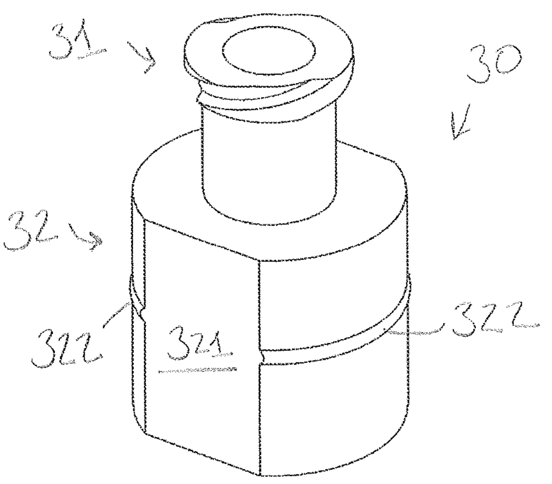
FIG. 7 is a perspective view of a tip cap according to one embodiment of the present invention.
Figure 8:
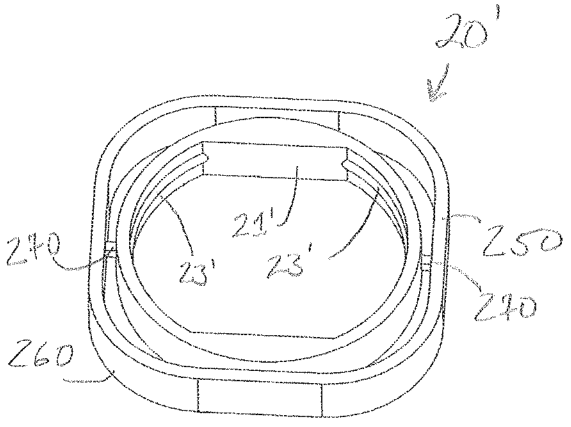
FIG. 8 is a perspective view of an inner ring according to another embodiment of the present invention.
Figure 9:
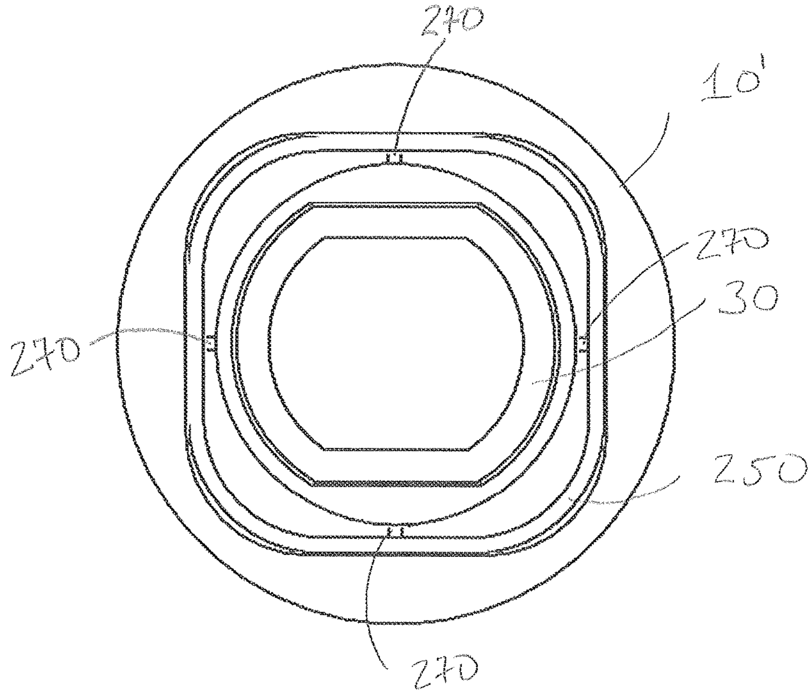
FIG. 9 is a bottom view of an inner ring placed within an outer cover according to another embodiment of the present invention.

FIGS. 7-9 depict an alternative embodiment for a torque limiting arrangement in a tamper evident cap 1. In the depicted embodiment, the tip cap 30 is substantially similar, but the inner ring 20' and outer cover 10' are configured to support a frangible arrangement. In particular, the inner ring 20' includes multiple components: a tip cap engaging ring 250, an outer cover engaging ring 260, and a plurality of frangible members 270. The tip cap engaging ring 250 includes one or more flats 21' and an interference ring 23'. The flats 21' are dimensioned and configured to engage against flats 321 on the tip cap to support rotation of both the tip cap 30 and inner ring 20' as a single unit. The tip cap engaging ring 250 is connected to the outer cover engaging ring 260 via a plurality of frangible members 270. The outer cover engaging ring 260 is substantially rectilinear and is dimensioned to nest within the inner periphery of the outer cover 10', which substantially conforms to the rectilinear configuration of the outer cover engaging ring 260. In a preferred embodiment, the frangible members 270 are dimensioned and configured to break once a predetermined torque has been applied to the tip cap 30 by the syringe, thereby ensuring that the user does not over tighten the tip cap 30 on the syringe. In a preferred embodiment, the predetermined torque value is a maximum recommended tightening torque of the syringe. As will be understood, once the frangible members 270 are broken, the tip cap 30 will rotate freely within the outer cover 10', thereby preventing the tip cap 30 from being unscrewed.

Figure 10:
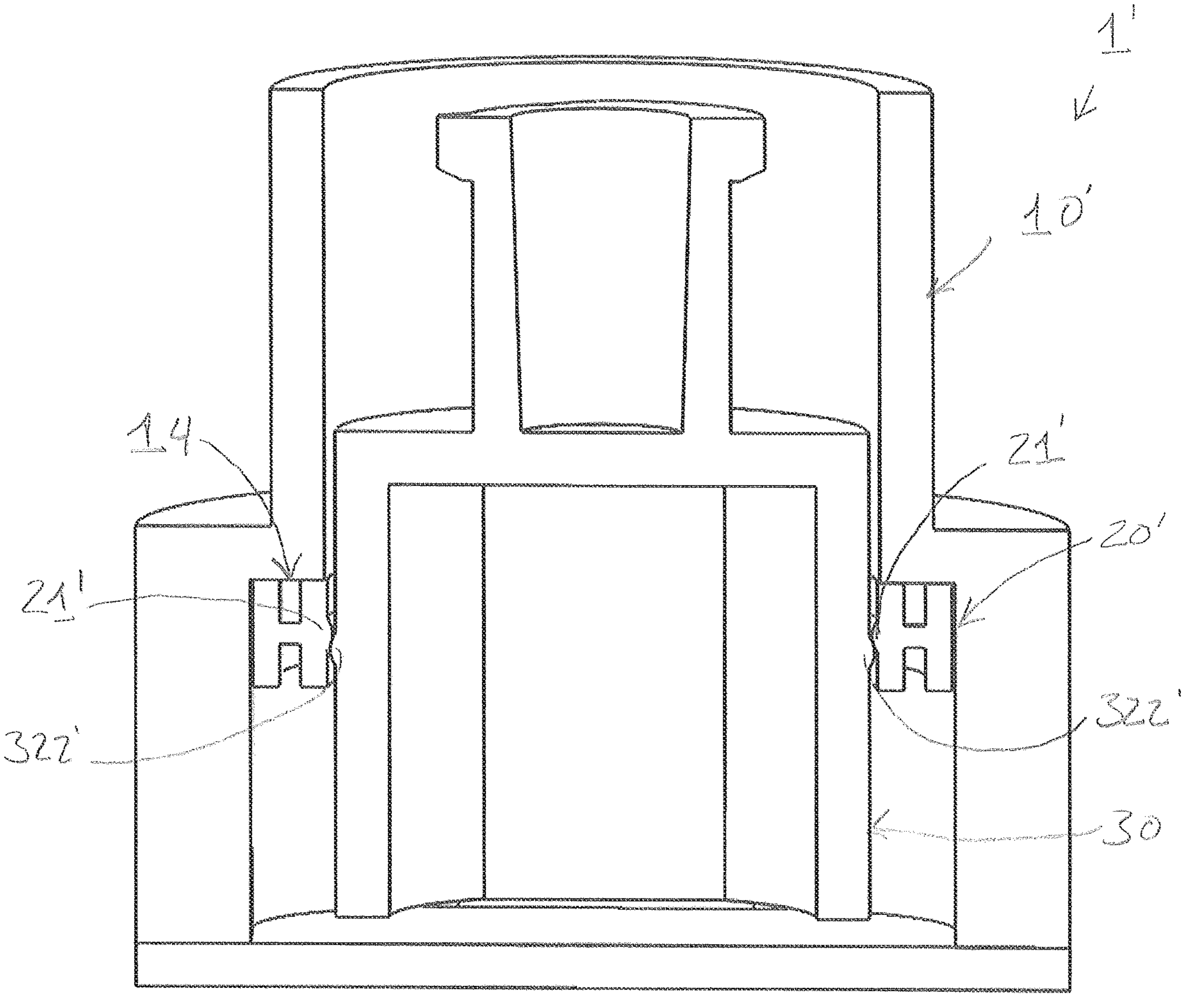
FIG. 10 is a section view of a tamper evident cap according to another embodiment of the present invention.

FIG. 10 is a section view of the embodiments of FIGS. 7-9 depicting the interaction of the interference rings 23, 322. It should be appreciated that this interaction may also be applied to any other embodiment, including the embodiments of FIGS. 1-6. In the depicted embodiment, the interference rings, 23, 322, comprise bosses on the inner periphery of the inner ring 20 and the outer periphery of the tip cap 30. However, alternative constructions may be applicable. By way of non-limiting example, the interference rings may also comprise a boss on one component and a channel on the other component, which would tend to restrict the inner ring 20 from translating along the tip 14 cap 30 until the tip cap 30 is removed from the outer cover 10. As can be seen, when in an operative disposition, the inner ring 20' is held between the interference ring 322 of the tip cap 30 and the shoulder 14 of the outer cover 10'. The interference ring 23' of the inner ring 20' rests against the interference ring 322 of the tip cap 30. This arrangement holds the outer cover 10' in place over the tip cap 30. When the tamper evident cap is to be removed from the syringe, the user will withdraw the tip cap 30 from the outer cover 10' by applying enough force to overcome the interference of the interference rings 23, 322. When this occurs, the inner ring 20' will be free to move within the outer cover 10'. As such, if the outer cover 10' were to be replaced over the tip cap 30, the inner ring 20 would not slip over the interference ring 322 of the tip cap 30, and instead may simply be pushed further into the outer cover 10 (if not already resting on the bottom of the outer cover). Therefore, a user may be able to easily discern whether the outer cover 10' had been previously removed, thus providing a tamper evident feature.

Since many modifications, variations and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A tamper evident cap comprising:
at least an outer cover, a tip cap, and an inner ring;
said tip cap being dimensioned and configured to receive said inner ring circumferentially around an inner ring engaging portion of said tip cap;
said tip cap and said inner ring being cooperatively dimensioned to rotate together when a torque is applied to said tip cap, and
said inner ring including at least one flat and said inner ring engaging portion of said tip cap including at least one flat.

2. The tamper evident cap as recited in claim 1 wherein said inner ring includes a plurality of biased fingers.

3. The tamper evident cap as recited in claim 1 wherein said inner ring includes a plurality of frangible members.

4. A tamper evident cap comprising:
at least an outer cover, a tip cap, and an inner ring;
said tip cap including a tip engaging portion dimensioned and configured to receive a syringe tip, as well as an inner ring engaging portion, said inner ring engaging portion including at least one flat and an interference ring;

said inner ring including at least one flat, and interference ring, and a plurality of biased fingers, said outer cover including a plurality of ring engaging members and a shoulder;

said inner ring being disposed on said inner ring engaging portion of said tip cap having said flat of said inner ring engaged against said flat of said tip cap; and said inner ring being further disposed with said interference ring of said inner ring being disposed between said interference ring of said tip cap and said shoulder of said outer cover.

5. The tamper evident cap as recited in claim 4 wherein said tip engaging portion is configured as a luer taper.

6. The tamper evident cap as recited in claim 4 wherein said plurality of biased fingers and said plurality of ring engaging members are dimensioned and configured to abut one another.

7. The tamper evident caps as recited in claim 6 wherein said plurality of biased fingers and said plurality of ring engaging members are dimensioned and configured to support transmission of torque when said tip cap is rotated in a first direction and further configured to slip when said tip cap is rotated in a second direction.

* * * * *